United States Patent [19]

Pande

[11] Patent Number: 4,753,765

[45] Date of Patent: * Jun. 28, 1988

[54] METHOD OF MAKING A CATHETER HAVING A FUSELESS TIP

[75] Inventor: Gyan S. Pande, Miramar, Fla.

[73] Assignee: Cordis Corporation, Miami, Fla.

[*] Notice: The portion of the term of this patent subsequent to Jan. 13, 2004 has been disclaimed.

[21] Appl. No.: 836,338

[22] Filed: Mar. 5, 1986

Related U.S. Application Data

[60] Division of Ser. No. 587,382, Mar. 8, 1984, Pat. No. 4,596,563, which is a continuation-in-part of Ser. No. 502,526, Jun. 9, 1983, abandoned.

[51] Int. Cl.⁴ .................. B29C 47/06; B29C 63/22
[52] U.S. Cl. ................... 264/149; 264/150; 264/167; 264/173; 425/132; 604/264
[58] Field of Search .............. 264/173, 150, 149, 167, 264/172, 139; 604/264; 425/132

[56] References Cited

U.S. PATENT DOCUMENTS

| | | |
|---|---|---|
| 2,561,569 | 7/1951 | Flynn .................. 264/149 |
| 2,810,424 | 10/1957 | Swartswelter et al. . |
| 2,934,514 | 4/1960 | Salyer et al. . |
| 3,336,918 | 8/1967 | Jeckel . |
| 3,485,234 | 12/1969 | Stevens . |
| 3,561,493 | 2/1971 | Maillard et al. . |
| 3,618,614 | 11/1971 | Flynn . |
| 3,724,985 | 4/1973 | Burlis et al. .................. 425/132 |
| 3,911,927 | 10/1975 | Rich et al. . |
| 3,924,632 | 12/1975 | Cook . |
| 4,056,344 | 11/1977 | Lemelson .................. 425/132 |
| 4,066,743 | 1/1978 | Kneller . |
| 4,125,599 | 11/1978 | Wiegert . |
| 4,160,015 | 7/1979 | Wiegert . |
| 4,182,787 | 1/1980 | Goossens et al. . |
| 4,191,185 | 3/1980 | Lemieux . |
| 4,195,637 | 4/1980 | Gruntzig et al. . |
| 4,211,741 | 7/1980 | Ostoich . |
| 4,250,072 | 2/1981 | Flynn . |
| 4,276,250 | 6/1981 | Satchell et al. .................. 264/167 |
| 4,282,876 | 8/1981 | Flynn . |
| 4,283,447 | 8/1981 | Flynn . |
| 4,306,562 | 12/1981 | Osborne . |
| 4,321,226 | 3/1982 | Markling .................. 264/149 |
| 4,330,497 | 5/1982 | Agdanowski .................. 264/139 |
| 4,430,083 | 2/1984 | Ganz et al. . |
| 4,495,134 | 1/1985 | Ouchi et al. .................. 264/248 |
| 4,551,292 | 11/1985 | Fletcher et al. .................. 264/173 |
| 4,636,346 | 1/1987 | Gold et al. .................. 264/149 |

FOREIGN PATENT DOCUMENTS

58-11118 1/1983 Japan .................. 264/173

Primary Examiner—Jeffery Thurlow
Attorney, Agent, or Firm—Lockwood, Alex, Fitzgibbon & Cummings

[57] ABSTRACT

A method is providing for making a thin-walled catheter of the type having a distal end adapted to be formed into a curve and guided through branching blood vessels or the like so that the catheter is provided with a two-layered tubular body portion having a rigid inner sheath and a flexible outer sheath, which may be radiopaque. The catheter exhibits excellent torque response and control while being especially thin-walled, thereby permitting minimization of the outer diameter size while providing excellent liquid flow rates therethrough and excellent strength properties. The tip portion is fuseless with respect to the rest of the catheter, the tip portion being an integral extension of the flexible outer sheath that is formed over a gap between lengths of the rigid inner sheath.

4 Claims, 1 Drawing Sheet

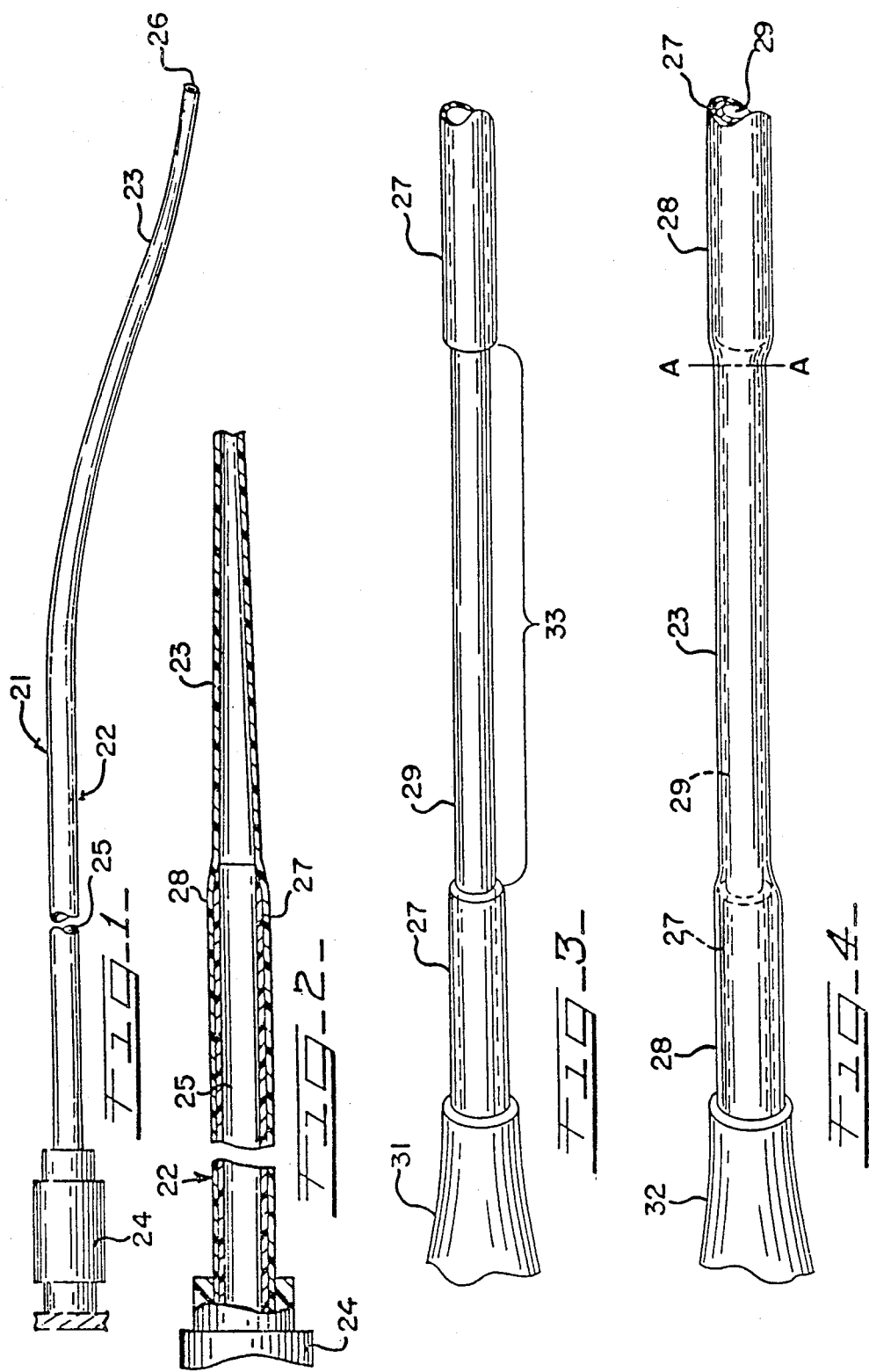

METHOD OF MAKING A CATHETER HAVING A FUSELESS TIP

This is a divisional of application Ser. No. 587,382, filed Mar. 8, 1984, now U.S. Pat. No. 4,596,563, which is a continuation-in-part of application Ser. No. 502,526, filed June 9, 1983, abandoned.

BACKGROUND AND DESCRIPTION OF THE INVENTION

The present invention generally relates to a thin-walled catheter and method for making same, and more particularly, to a catheter that is thin-walled while still exhibiting excellent strength and torque response characteristics, the thin-walled construction being one in which a thin flexible outer sheath overlies a thin rigid inner sheath to thereby form the elongated tubular portion of the catheter. The catheter further includes a flexible, atraumatic tip portion located at one end of the elongated tubular member and that is a fuseless, integral extension of the flexible outer sheath that is formed at a gap between lengths of the rigid inner sheath.

Catheters such as intravascular catheters are well known for use in diagnostic and therapeutic applications wherein it is necessary to administer a fluid to, or otherwise contact, a precise location within the cardiovascular system, for example, by guiding the tip or distal end of the catheter through branching blood vessels. Such guiding is accomplished in part by manipulation of a proximal portion of the catheter in order to impart forces needed to curve and guide the catheter through the curving and branching blood vessels.

Because these types of catheters are used in an intravascular manner, they must have an extremely small outside diameter. Inasmuch as such catheters typically come into contact with living tissue, including organs such as the heart, it is extremely important that the catheter be in place for a minimal length of time. The overall insertion time includes the length of time needed to transmit the therapeutic or diagnostic fluid through the length of the catheter. This flow velocity is dependent upon the internal diameter of the catheter, as well as the strength of the catheter which limits the pressure that can be applied in order to transmit the fluid therethrough. It is also important that these catheters be very resistant to the formation of kinks therein which requires a certain degree of stiffness, while at the same time possessing adequate flexibility to be responsive to maneuvering forces and to be as atraumatic as possible.

Catheters that require a relatively stiff inner lumen can advantageously utilize these properties. Included are intravascular catheters, guiding catheters through which balloon catheters for angioplasty techniques and the like can be passed, and sheaths where wall thinness and strength are particularly important.

The present invention provides a catheter that has an elongated tubular portion having an internal layer that is a rigid layer which exhibits strength and stiffness properties that are extremely advantageous for an intravascular catheter or the like while still having adequate flexibility in its thin-walled sheath condition to permit the flexibility required of such a catheter. Closely overlying, and typically extruded onto, the rigid inner sheath is a flexible outer sheath that is compatible with the rigid inner sheath and that, as a layer over the rigid inner sheath, imparts improved atraumatic properties to the catheter and contributes to the overall flexibility of the unitary device, while also providing convenient opportunities to impart radiopaque properties to the catheter. These catheters, which are preferably produced by extrusion techniques including coextrusion when appropriate, have a flexible tip portion that is a fuseless, integral extension of the flexible outer sheath.

By this combination, it has been discovered that the advantages of a multi-walled catheter are achieved while at the same time providing a fuselessly tipped catheter that has the thin-walled properties often associated with catheters having single-layered walls, including the atraumatic and flexibility attributes normally associated therewith.

Accordingly, a general object of the present invention is to provide an improved fuselessly tipped thin-walled catheter.

Another object of the present invention is to provide a thin-walled catheter that is especially suitable for highly delicate treatments and diagnostic procedures including coronary angiography, angioplasty, ventricular and aortic flush injections, and other similar procedures within the cardiovascular system.

Another object of the present invention is to provide an improved thin-walled catheter and method of making same which utilizes a polycarbonate material as a thin-walled extrusion having flexibility suitable for intravascular catheters and the like, while still retaining its highly advantageous strength properties.

Another object of this invention is an improved method for forming a thin-walled catheter which includes fuselessly forming a tip portion that is integral with an outer flexible sheath and that is extruded over a gap in an inner rigid sheath.

Another object of the present invention is to provide an improved thin-walled catheter that has an inner layer and an outer layer of extruded material and that does not require adding any strands of strengthening material therebetween. Another object of the present invention is the utilization of a polycarbonate material in a thin-walled form within the elongated tubular member of a catheter such as an intravascular catheter.

Another object of the present invention is to provide an improved intravenous catheter and method of producing same with a flexible, atraumatic fuselesstip that has high visibility under flouroscopy.

Another object of the present invention is to provided an improved intravascular catheter that exhibits excellent torque response or control and that is particularly resistant to kinking, while still possessing the atraumatic properties needed for an intravascular catheter.

These and other objects, features and advantages of the present invention will be clearly understood through a consideration of the following detailed description.

BRIEF DESCRIPTION OF THE DRAWINGS

In the course of this description, reference will be made to the attached drawings, wherein:

FIG. 1 is an elevational view, partially broken away, of a typical catheter of the intravascular type incorporating the present invention;

FIG. 2 is a partial, longitudinal cross-section, further broken away, of the catheter illustrated in FIG. 1;

FIG. 3 is a perspective view illustrating an extruded rigid inner sheath according to this invention and a tip-accommodating gap therein; and FIG. 4 is a perspective view illustrating the extrusion of the flexible polymer outer sheath over the rigid inner sheath illustrated in FIG. 3 and over the gap to form a fuseless flexible tip.

DESCRIPTION OF THE PARTICULAR EMBODIMENTS

FIG. 1 provides an illustration of the type of catheter, generally designated as 21, within which this invention is utilized, the illustrated catheter 21 being an intravascular catheter. Catheter 21 includes an elongated tubular member or body 22, a fuseless tip portion 23, and a hub member 24. A longitudinal bore 25 extends throughout the elongated tubular member 22 and the hub member 24, terminating in a distal orifice 26, which is the location at which, for example, diagnoses are made or therapeutic fluids are administered.

The elongated tubular member or body 22 includes a rigid inner sheath 27 and a flexible outer sheath 28. Each sheath 27 and 28 is extremely thin-walled to the extent that the elongated tubular member or body 22 is itself thin-walled in order to provide the bore 25 with a particularly large diameter in relation to the outer diameter of the elongated tubular member or body 22.

Rigid inner sheath 27 is an extrusion grade polymeric cylinder that had been formed by extrusion, preferably onto a precision mandrel 29, which is typically a silver wire or the like. This is illustrated generally in FIG. 3, depicting an outlet die 31 of an extruder. The rigid inner sheath 27 may be made of a rigid polymeric material such as polycarbonate, hard polyesters, hard polyurethanes, hard polyamides or nylons, high density polyethylene, or the like. Typically, such rigid polymeric materials will have a hardness between approximately Shore D75 and Shore D85. Polycarbonate is the preferred material out of which the rigid inner sheath 27 is made.

Flexible outer sheath 28 is a polymeric material that had been extruded as a sheath over the inner sheath 27. FIG. 4 depicts this flexible outer sheath eminating from an outlet die 32 of an extrusion molding device. The flexible outer sheath 28 may be made of a flexible polymeric material such as soft polyurethanes, soft polyester, low density polyethylene, or the like. Typically, such flexible polymeric materials will have a hardness between approximately Shore D40 and Shore D60. Polyurethane is the preferred material out of which the flexible outer sheath 28 is made.

Tip portion 23 is designed to minimize intimal trauma. It is extruded integrally with and made of the same polymeric material as the flexible outer sheath 28, whereby the tip portion 23 is a fuseless continuation and extension of the flexible outer sheath 28.

Because the tip portion 23 excludes the rigid, stiffening polymeric sheath 27, this results in a tip portion 23 that is particularly movable, flexible and atraumatic. Tip portion 23 is an integral extension of the flexible outer sheath 28, and it will take the shape needed for the particular catheter, including a generally straight configuration as illustrated in FIG. 1, so-called pigtail shaped curves, and specially designed curves for particular uses such as visceral curves and cerebral curves. Tip portion 23 may include openings other than the distal orifice 26. The particular shape of the tip portion 23 is formed by a suitable procedure, such as immersing the tip portion 23 in boiling water while bent as desired before removal of the precision mandrel 29.

The tip portion 23 is provided as an integral extension of the flexible outer polymeric sheath 28, and such is accomplished by extruding the flexible outer sheath 28 and the tip portion 23 together, the sheath portion 28 thereof being extruded over the rigid inner sheath 27, and the tip portion thereof being extruded directly onto the precision mandrel 29. A particularly advantageous manner of accomplishing this is as follows.

The rigid inner sheath 27, which is extruded onto the precision mandrel 29, is modified so as to impart a gap substantially equal to the length of the desired tip member, to thereby form a series of intermittent gaps between lengths of rigid polymer inner sheath on the precision mandrel 29, which lengths are the same as those desired for the body portions 22 of the particular catheters being produced. A layer of flexible polymer is extruded over the thus formed rigid polymer lengths and intermittent gaps therebetween in order to thereby extrude the flexible polymer material as an integral length that alternately overlies the rigid polymer inner sheath 27 and the precision mandrel 29. The portion of this flexible polymer extrusion that overlies the rigid polymer inner sheath 27 completes the formation of the elongated tubular member or body 22, while the portion of this flexible polymer extrusion that overlies the precision mandrel 29 forms the tip portion 23.

Each length of flexible polymer is subsequently severed at or near one end of the gap length, such as along line A—A of FIG. 4, in order to thereby provide an elongated tubular member 22 having a rigid polymer inner sheath 27 and a flexible polymer outer extrusion that extends beyond the rigid inner sheath 27 for a distance needed to provide the desired tip portion 23. This procedure eliminates the need for a separate bonding step and assures a smooth interface between the tip portion 23 and the body 22.

With more particular reference to the modification of the rigid polymer inner sheath so as to impart a plurality of gaps having a length substantially equal to the length of the desired tip member, two different general approaches may be taken. One includes removal of extruded rigid polymer and the other includes extruding the rigid polymer in an intermittent manner.

When proceeding by the removal approach, the rigid polymer coating or sheath is extruded continuously over the mandrel 29. Thereafter, the rigid polymer coating is removed from the mandrel 29 at predetermined gap lengths 33 (FIG. 3). Removal is effected in any convenient manner, including mechanical cutting, solvent dissolving, and ultrasonic removal (typically preceded by freezing). When proceeding by the intermittent extrusion approach, extrusion of the rigid inner coating proceeds until the needed length of body 22 has been coated onto the mandrel 29, at which time this extruding is interrupted or stopped while the mandrel 29 proceeds to move beyond the outlet die 31 in order to form a gap 33, after which extrusion resumes until another body length of rigid polymer coats the mandrel 29. Whether the removal approach or the intermittent extrusion approach is used, the flexible polymer is then coated over the body lengths and over the gaps, as illustrated in FIG. 4. The intermittent extrusion approach provides a possibility of simultaneous coextrusion of the inner, gapped coating and of the outer continuous coating.

In order to be suitable for use in procedures utilizing radiological techniques, such as those in which intravascular catheters are used, the catheter 21 should be radiopaque. An exemplary manner of imparting this property to the catheter 21 is to utilize a flexible polymer material that includes a radiopaque agent, such as barium sulfate or the like. This approach provides what can be an advantageous feature for many uses, which is that the tip portion 23 will be more visible by radiological techniques than the rest of the catheter 21, which enables the user to more easily focus on manipulations needed to maneuver the tip portion through the cardiovascular system.

When the outer sheath 28 is extruded over the inner sheath 27 as illustrated in FIG. 4, particularly advantageous results are obtained when the inner sheath 27 is in a heated condition, for example between about 300° and 400° F. when the rigid polymer is polycarbonate. Such heating softens the surface of the polycarbonate sheath 27 in order to enhance the combining of the outer sheath 28 with the inner sheath 27 to the extent that they are generally adhered together in order to form a more unitary body 22 that will be especially responsive to torque forces imparted thereto and will exhibit enhanced thin-walled properties.

With reference to the hub member 24, such will typically be joined to the proximal end of the elongated tubular member or body 22 by a suitable material, such as an adhesive or solvent that is a solvent for both materials of the inner and outer sheaths, as well as for the material of the hub member, which is typically a polycarbonate, whereby the respective materials will soften and adhere to each other. Suitable solvents include tetrahydrofuran, methylethylketone, acetone, or the like.

Hub portion 24 is of a structure that is suitable for the catheter use desired. Typically, such a hub portion 24 will be attached to an injector (not shown) to impart a force to the fluids being administered in order to pass same through the bore 25 and out of the distal orifice 26. This hub member 24 may, for example, take the form of a conventional female needle fitting. Also associated with the hub member may be a manipulator device (not shown) of known construction for rotating and/or deflecting the catheter as desired in order to assist in threading the tip portion 23 through branching blood vessels and the like.

An exemplary catheter 21 prepared according to this invention is an intravascular catheter of the "French 5" size that is extruded to a total wall thickness of the elongated tubular member or body 22 of approximately 0.008 inch. The inner sheath 27 layer thereof, if made of polycarbonate, would have a wall thickness range of on the order to about 0.0035 to 0.005 inch, depending upon the strength and stiffness desired. The corresponding wall thickness range of the outer sheath 28, if made of polyurethane, would be between about 0.0045 and 0.003 inch. Intravascular catethers of these dimensions and of the structure according to this invention have a burst pressure of on the order of up to about 1,200 psi or greater.

It will be understood that the embodiments of the present invention which have been described are merely illustrative of a few of the applications of the principles of the present invention. Numerous modifications may be made by those skilled in the art without departing from the true spirit and scope of the invention.

I claim:

1. A method of making a fuseless catheter having a distal end adapted to be formed into curved configurations and guided through branching blood vessels, the method comprising:

extruding a longitudinal axially gapped rigid polymer elongated cylindrical inner sheath coating radially onto a mandrel, wherein said extruding step includes intermittently extruding the rigid polymer coating, thereby providing a longitudinal axially extending cylindrical gap between longitudinal axial lengths of the rigid polymer elongated inner sheath coating and forming a longitudinal, generally axial inner bore through the rigid polymer longitudinal lengths, said longitudinal axially extending cylindrical gap exposing an axial length of the mandrel;

extruding, while the longitudinal axially extending cylindrically gapped rigid polymer elongated inner sheath coating is on a mandrel, a flexible polymer elongated cylindrical outer sheath coating radially onto and closely overlying the rigid polymer longitudinal inner sheath coating lengths to thereby provide an elongated two-layered cylindrical tubular member;

said latter extruding step lays down a continuous and uninterrupted flexible polymer elongated sheath coating continuously extending beyond the elongated two-layered tubular member to form a single-layered fuseless atraumatic tip portion radially on the mandrel at said cylindrical gap without fusing said atraumatic tip portion to said two-layered cylindrical tubular member, and said fuseless atraumatic tip portion is integral with the flexible polymer elongated outer sheath coating and has an inner bore therethrough that is generally coextensive with the longitudinal, generally axial bore of the rigid polymer inner sheath coating;

said step of extruding the outer flexible polymer elongated sheath coating includes laminating same to the inner rigid polymer elongated sheath coating; and severing the fuseless atraumatic tip portion at a location generally along an end of the longitudinal axially extending cylindrical gap.

2. The method according to claim 1, wherein said longitudinally gapped rigid polymer elongated inner sheath coating and said flexible polymer elongated sheath coating are coextruded.

3. The method according to claim 1, further including heating the inner, rigid polymer elongated sheath coating no later than said step of extruding the outer, flexible polymer elongated sheath coating onto the inner, rigid polymer elongated sheath coating.

4. The method according to claim 1, further including treating the inner, rigid polymer elongated sheath coating for adhering same to the outer, flexible polymer elongated sheath coating.

* * * * *